United States Patent [19]

Sismondi et al.

[11] Patent Number: 5,066,672

[45] Date of Patent: Nov. 19, 1991

[54] POLYFLUOROALKYL ACETATES, THIOACETATES AND ACETAMIDES, AND THEIR APPLICATIONS

[75] Inventors: Alain Sismondi; Parfait Abenin; Aimé Cambon, all of Nice, France

[73] Assignee: Societe Atochem, France

[21] Appl. No.: 457,565

[22] Filed: Dec. 27, 1989

[30] Foreign Application Priority Data

Dec. 27, 1988 [FR] France .................. 88 17240

[51] Int. Cl.$^5$ .............. A01N 37/00; C07C 69/74; C07C 327/00; C07C 229/00
[52] U.S. Cl. ................... 514/513; 560/128; 560/155; 558/251; 558/255; 558/256; 514/529; 514/534
[58] Field of Search ........... 560/128, 155; 558/251, 558/255, 256; 514/513, 529, 534

[56] References Cited

U.S. PATENT DOCUMENTS

| | | | |
|---|---|---|---|
| 3,510,494 | 5/1970 | Gagliardi | 558/251 |
| 3,563,999 | 2/1971 | Anello et al. | 558/251 |
| 4,049,668 | 9/1977 | Szur | 558/251 |
| 4,107,055 | 8/1978 | Sukornick et al. | 558/251 |
| 4,658,052 | 4/1987 | Ramlock et al. | 558/251 |

FOREIGN PATENT DOCUMENTS 1438617  4/1966  France .................. 558/251

Primary Examiner—Mary C. Lee
Assistant Examiner—Robert C. Whittenbaugh
Attorney, Agent, or Firm—Morgan & Finnegan

[57] ABSTRACT

The invention relates to compounds of the polyfluoroalkyl acetate, thioacetate or acetamide type, which can be denoted by the general formula:

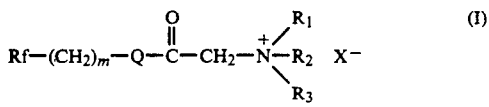

in which Rf denotes a perfluoroalkyl radical, m is an integer ranging from 1 to 4, Q denotes an oxygen or sulphur atom or an NH group, $X^-$ denotes an anion, $R_1$ denotes an alkyl radical containing from 1 to 3 carbon atoms, $R_2$ denotes the allyl radical or an alkyl radical containing from 1 to 18 carbon atoms, and $R_3$ denotes an alkyl radical containing from 7 to 18 carbon atoms or one of the following radicals:

$$-(CH_2)_n-S-(CH_2)_m-Rf$$

$$-(CH_2)_n-O-CO-C(R)=CH_2$$

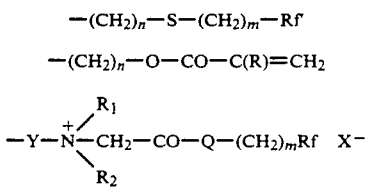

wherein n is an integer from 2 to 4, R is hydrogen or methyl, and Y denotes $C_2-C_8$ alkylene bridge optionally interrupted by an oxygen atom.

These compounds can be used as surface-active agents or an monomers for developing artificial vesicles.

4 Claims, No Drawings

POLYFLUOROALKYL ACETATES, THIOACETATES AND ACETAMIDES, AND THEIR APPLICATIONS

FIELD OF THE INVENTION

The present invention relates to new polyfluorinated compounds. Its subject matter is more particularly substituted compounds of the acetate, thioacetate or acetamide type which can be used especially as surface-active agents, or as "monomers" for developing artificial vesicles.

BACKGROUND OF THE INVENTION

Many fluorinated surfactants are already known, and in particular quaternary ammonium salts in which a perfluorinated radical is linked to the quaternary ammonium group (for example trialkylammonium or pyridinium) by a bridge whose nature greatly affects the application properties. This bridge can be very simple, for example $CH_2$ or $C_2H_4$ (U.S. Pat. No. 2,727,923 and French Patent No. 1,588,482) or more complex, for example $-C_2H_4SONH(CH_2)_3-$ (French Patent No. 2,084,888) or $-C_2H_4S(CH_2)_3-OCH_2CH(OH)CH_2-$ (European Patent No. 256,980), and the like. The above references are hereby incorporated by reference.

DETAILED DESCRIPTION OF THE INVENTION

The subject matter of the present invention is now a new class of polyfluorinated compounds which can be denoted by the general formula:

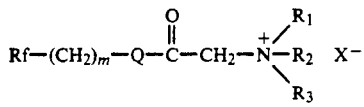   (I)

in which Rf denotes a linear of branched perfluoroalkyl radical containing from 2 to 16 carbon atoms, m is an integer ranging from 1 to 4, preferably equal to 2, Q denotes an oxygen or sulphur atom or an NH group, $X^-$ denotes a monovalent anion or its equivalent, $R_1$ denotes an alkyl radical containing from 1 to 3 carbon atoms, $R_2$ denotes allyl or a linear or branched alkyl radical containing from 1 to 18 carbon atoms, and $R_3$ denotes a linear or branched alkyl radical containing from 7 to 18 carbon atoms or one of the following radicals:

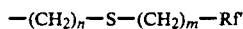   (II)

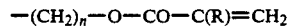   (III)

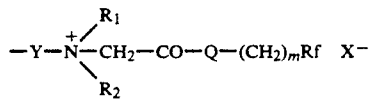   (IV)

wherein the symbols m, $R_1$, $R_2$, Q, Rf and $X^-$ have the same meanings as above, n is an integer ranging from 2 to 4, R denotes a hydrogen atom or a methyl radical, Y denotes an alkylene bridge of 2 to 8 carbon atoms optionally interrupted by an oxygen atom, and Rf' denotes a linear or branched perfluoroalkyl radical containing from 2 to 16 carbon atoms. The radicals Rf and Rf' may be identical or different and are preferably linear perfluoroalkyl radicals containing 4, 6, 8 or 10 carbon atoms.

The compounds of formula (I) can be prepared starting from the haloacetates, -thioacetates and -acetamides of formula:

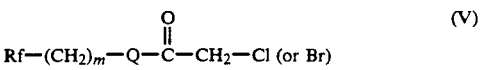   (V)

some of which are already known (French Patent No. 1,438,617 and U.S. Pat. No. 4,107,055) and which can be obtained by reaction of a haloacetyl halide of formula:

   (VI)

where each of Z and Z', which are identical or different, denotes a chlorine or bromine atom with a polyfluoroalkanol $Rf-(CH_2)_m-OH$, a polyfluoroalkanethiol $Rf-(CH_2)_m-SH$ or a polyfluoroalkylamine $Rf-(CH_2)_m-NH_2$. The two reactants can be used in equimolar quantities, but it is generally advantageous to employ a slight excess of halide (VI).

When a polyfluoroalkanol or a polyfluoroalkanethiol is the starting material for preparing the compounds of formula (V) in which Q denotes an oxygen or sulphur atom respectively, the reaction may be carried out at a temperature of between 20° and 70° C., under an inert gas atmosphere, in the absence of solvent or in an anhydrous organic solvent, for example, an ether, a halogenated hydrocarbon or acetonitrile. However, the addition of the reactants must take place while the mixture is cooled to a temperature of between $-5$ and $+10°$ C., preferably between approximately 0° and 5° C. The reactor must also be fitted with a device which permits trapping the hydrochloric or hydrobromic acid released during the reaction. At an equivalent number of carbon atoms, the reaction is faster with a polyfluoroalkanethiol than with a polyfluoroalkanol. The polyfluoroalkyl 2-haloacetates or thioacetates thus obtained may be used as such or, if need be, purified by distillation.

When a polyfluoroalkylamine is the starting material for preparing the compounds (V) in which Q denotes an NH group, the reaction is carried out in the presence of a base permitting the hydrochloric or hydrobromic acid formed to be fixed. The bases used may be, for example, tertiary amines such as triethylamine and pyridine, alkali metal carbonates and alkali metal hydroxides The reaction may be carried out at a temperature of between 20° and 50° C., under an inert gas atmosphere, in an anhydrous organic solvent, for example, an ether, a halogenated hydrocarbon, or an aromatic hydrocarbon. As in the case of polyfluoroalkanols and of polyfluoroalkanethiols, the addition of the reactants must take place while the reaction mixture is cooled to a temperature of between $-5°$ and $+10°$ C., preferably approximately between 0° and 5° C. The N-polyfluoroalklyl-2-haloacetamides thus obtained may be used as such or after recrystallization, for example, from petroleum ether.

The polyfluoroalkanols $Rf-(CH_2)_m-OH$, the polyfluoroalkanethiols $RF-(CH_2)_m-SH$ and the polyfluoroalkylamines $RF(CH_2)_m-NH_2$ are well-known compounds, See, for example, the following patents (incorporated by reference):

Polyfluoroalkanols: French Patent No. 1,380,579, U.S. Pat. Nos. 3,083,224; 3,145,222; and 3,285,975

Polyfluoroalkanethiols: U.S. Pat. Nos. 2,894,991; 3,088,849; 3,544,633; French Patent Nos. 1,221,415 and 2,083,422

Polyfluoroalkylamines: German Patent No. 1,768,939, French Patent No. 1,532,284, Japanese Patent No. 77-118,406 and U.S. Pat. No. 3,257,407.

The compounds of formula (V) are extremely reactive towards nucleophiles. They permit substitution reactions without any risk of undergoing an elimination reaction resulting in the formation of unsaturated by-products.

The compounds of formula (I) in accordance with the present invention can be prepared by reaction of a compound of formula (V) with the corresponding tertiary amine. The synthesis is carried out by using stoichiometric quantities of compound (V) and of the chosen amine. It is possible for these reactants to be optionally dissolved in 2 to 3 volumes of ether. An exothermic reaction takes place, with the formation of a quaternary ammonium bromide or chloride.

The reaction time and the physical appearance of the salts formed vary depending on the nature of the chosen amine. All these salts are water-soluble and the majority have a crystalline structure.

As examples of amines which can be used, there may be mentioned, no limitation being implied, N,N-dimethylalkylamines in which the alkyl radical contains from 7 to 18 carbon atoms, N-methyldialkylamines in which the alkyl radicals contain 7 to 18 carbon atoms, N-methyl-N-allylalkylamines in which the alkyl radical contains from 7 to 18 carbon atoms, N,N-dimethylaminoalkyl acrylates and methacrylates, as well as the fluorinated amines of the type Rf'—(CH$_2$)$_m$—S—(CH$_2$)$_n$—N(CH$_3$)$_2$, which result in the quaternary ammonium salts of formula:

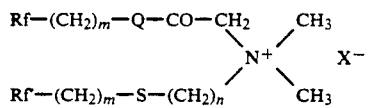

in which Q, m, n, Rf, Rf' and X have the same meanings as above.

An example of a tertiary diamine which can be used is N,N,N',N'-tetramethyl-ethylenediamine, which produces double salts of formula:

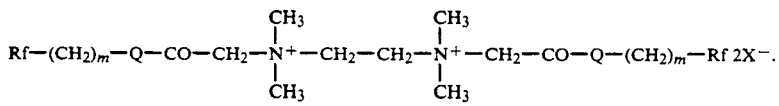

Other examples of tertiary diamines which can be used are N,N,N',N'-tetramethyl-1,6-hexamethyl-enediamine and N,N,N',N'-tetramethyldiaminodiethyl ether.

The bromide or chloride anion of the ammonium salts can be easily exchanged for another anion by methods which are well known per se. The iodide, nitrate, para-toluenesulphonate, sulphate, alkylsulphate and picrate anions may be mentioned as examples of other anions.

The ammonium salts according to the invention are valuable surface-active agents which can be used as additives in a very wide variety of fields, as wetting agents, emulsifiers, dispersants or foaming agents. Furthermore, they can be used as monomers for the development of artificial vesicles.

The preceding references are hereby incorporated by reference.

EXAMPLES

The following examples illustrate the invention without limiting it.

EXAMPLE 1

0.01 mole (2.64 g) of 2-perfluorobutylethanol C$_4$F$_9$—C$_2$H$_4$—OH is placed in a reactor fitted with a condenser, a dropping funnel and a device enabling HBr to be trapped. After the assembly has been purged with nitrogen and the reactor cooled to 0° C., 0.011 moles (2.22 g) of bromoacetyl bromide Br—CH$_2$—COBr dissolved beforehand in 15 ml of dry ethyl ether are added slowly via the dropping funnel. The mixture is then heated for 24 hours at 60° C. under an inert atmosphere and is then hydrolyzed and extracted with ethyl ether. The ether phases are washed copiously until the pH of the aqueous washing is neutral. The organic phase is then dried over anhydrous sodium sulphate. Then the solvent is evaporated off. The residue is distilled. In this was, 2-perfluorobutylethyl bromoacetate C$_4$F$_9$—C$_2$H$_4$—O—CO—CH$_2$—Br, which boils at 60° C. at 67 Pa is obtained in a 69% yield.

By proceeding in the same way, starting from the alcohol C$_6$F$_{13}$—C$_2$H$_4$—OH, 2-perfluorohexylethyl bromoacetate C$_6$F$_{13}$—C$_2$H$_4$—O—CO—CH$_2$—Br, which boils at 74° C. at 67 Pa, is obtained. Yield: 68%.

EXAMPLE 2

The procedure is as in Example 1, but with 0.01 mole of 2-perfluorobutylethanethiol C$_4$F$_9$C$_2$H$_4$SH replacing 2-perfluorobutylethanol and with heating being applied only for 12 hours at 40° C. instead of 24 hours at 60° C.

In this way, 2-perfluorobutylethyl bromothioacetate C$_4$F$_9$C$_2$H$_4$—S—CO—CH$_2$—Br, which boils at 61° C. at 133 Pa, is obtained in a 70% yield.

By proceeding in the same way, starting with the thiols C$_6$F$_{13}$C$_2$H$_4$SH and C$_8$F$_{17}$C$_2$H$_4$SH, the following bromothioacetates are obtained, respectively:

| | | |
|---|---|---|
| C$_6$F$_{13}$C$_2$H$_4$—S—CO—CH$_2$—Br | Bp 90° C./133 Pa | Yld: 68% |
| C$_8$F$_{17}$C$_2$H$_4$—S—CO—CH$_2$—Br | Bp 118° C./133 Pa | Yld: 72% |

EXAMPLE 3

0.015 moles of chloroacetyl chloride Cl—CH$_2$—COCl dissolved in 10 ml of dry ethyl ether are placed in a reactor fitted with a condenser and a dropping funnel. With the reactor cooled to 0° C., 0.01 mole of 2-perfluorohexylethylamine C$_6$F$_{13}$—C$_2$H$_4$—NH$_2$ and 0.01 mole of pyridine dissolved in 20 ml of dry ethyl ether are added via the dropping funnel. After returning to ambient temperature, the mixture is heated for 24 hours at 40° C. under an inert atmosphere. The reaction mixture is then acidified with a 50% strength solution of hydrochloric acid and is then extracted with ethyl ether. The organic phases are dried over anhydrous sodium sulphate and the ether is then evaporated off. The residue is distilled under reduced pressure or recrystallized from petroleum ether. In this way 2-perfluorohexylethyl-chloroacetamide: C$_6$F$_{13}$—C$_2$H$_4$—N-

H—CO—CH$_2$—Cl, which melts at 30° C., is obtained. Yield: 65%.

EXAMPLE 4

The procedure is as in Example 3, but with chloroacetyl chloride Cl—CH$_2$—COCl replaced with its bromo homologue Br—CH$_2$—COBr. The following bromoacetamide is obtained:

| | | |
|---|---|---|
| C$_6$F$_{13}$—C$_2$H$_4$—NH—CO—CH$_2$—Br | Bp = 85° C./133 Pa | Yld = 70% |

If, furthermore, 2-perfluorohexylethylamine is replaced with 2-perfluorobutylethylamine, the following bromoacetamide is obtained:

| | | |
|---|---|---|
| C$_4$F$_9$—C$_2$H$_4$—NH—CO—CH$_2$—Br | Bp = 80° C./133 Pa | Yld = 76% |

EXAMPLE 5

Salts of the following formulas were prepared from the bromo compounds described in Examples 1 (bromoacetates), 2 (bromothioacetates), and 4 (bromoacetamides) and from the amines NR$_1$R$_2$R$_3$ referred to in the second column of Tables (A), (B) and (C):

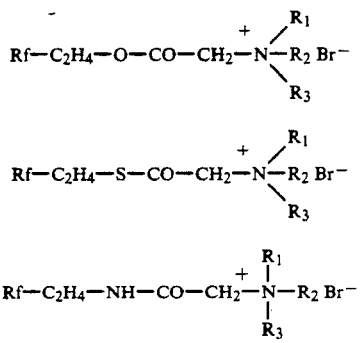

by proceeding as follows:

Equimolar quantities of amine NR$_1$R$_2$R$_3$ and of bromo compound, dissolved in 2 to 3 volumes of ethyl ether, are introduced into a reactor equipped with a condenser and fitted with a magnetic stirrer. Several cases arise, depending on the nature of the reactants:

In most cases, an immediate precipitation is observed in the form of a white solid. The reaction is forced to completion by heating the ether under reflux until all the bromide has been consumed. The precipitate is then filtered off, rinsed with ethyl ether and dried.

For some reactant combinations a turbidity appears very quickly. The solution is left to stand and a more or less viscous oil is recovered by phase separation and is washed with dry ethyl ether.

Lastly, in some other cases, neither precipitate nor apparent turbidity is observed. However, if the temperature is lowered between 0° and 10° C., a gel appears, which is swollen by solvent. After evaporation of the solvent, the expected ammonium is obtained in the form of a solid or of an oil.

Table A corresponds to the ammonium salts of formula (I-a) which are prepared from the bromoacetates of Example 1, Table B to the salts of formula (I-b) prepared from the bromothioacetates of Example 2, and Table C to the salts of formula (I-c) prepared from the bromoacetamides of Example 4. The first column of these tables states the identity of the perfluoroalkyl radical of the bromo compound used.

The fourth and fifth columns of these tables show, respectively, the surface tension γs and the interfacial (cyclohexane) tension γi of the ammonium salt in question, in mN/m, measured at 25° C. in 0.1% strength aqueous solution, unless shown otherwise by one of the following letters, in brackets:

i: 0.2% strength aqueous solution
j: 0.3% strength aqueous solution
k: 0.5% strength aqueous solution
l: 1% strength aqueous solution

TABLE A

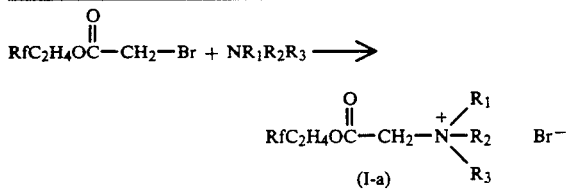

| | | COMPOUND I-a | | |
|---|---|---|---|---|
| Rf | Amine NR$_1$R$_2$R$_3$ | Yield (%) | γs | γi |
| C$_4$F$_9$ | N,N-Dimethylheptylamine | 95 | 16.7 (l) | 1.9 (l) |
| C$_6$F$_{13}$ | " | 97 | 15.3 (j) | |
| C$_4$F$_9$ | N,N-Dimethyloctylamine | 95 | 16.6 (j) | |
| C$_6$F$_{13}$ | " | 93 | 15.8 (j) | |
| C$_4$F$_9$ | N,N-Dimethylnonylamine | 95 | 16.7 (j) | |
| C$_6$F$_{13}$ | " | 93 | 15.5 (j) | 2.4 (j) |
| C$_4$F$_9$ | N,N-Dimethyldecylamine | 97 | 17.5 (j) | |
| C$_6$F$_{13}$ | " | 94 | 15.7 (j) | |
| C$_4$F$_9$ | N,N-Dimethyldodecylamine | 89 | 19.0 (l) | |
| C$_6$F$_{13}$ | " | 93 | 16.9 (j) | |
| C$_4$F$_9$ | N-Allyl-N-methyloctylamine | 98 | 16.6 (k) | |
| C$_6$F$_{13}$ | " | 78 | 15.1 (k) | |
| C$_4$F$_9$ | N-Allyl-N-methylnonylamine | 71 | 16.8 (k) | |
| C$_6$F$_{13}$ | " | — | 16.1 (k) | |
| C$_4$F$_9$ | N-Allyl-N-methyldecylamine | — | 17.4 (k) | |
| C$_6$F$_{13}$ | " | — | 15.8 (k) | |
| C$_4$F$_9$ | N-Allyl-N-methylundecylamine | — | 18.5 (k) | |
| C$_6$F$_{13}$ | N-Allyl-N-methylundecylamine | 74 | 17.1 (k) | |
| C$_4$F$_9$ | N-Allyl-N-methyldodecylamine | 91 | 19.7 (k) | |
| C$_6$F$_{13}$ | N-Allyl-N-methyldodecylamine | 84 | 18.0 (k) | |
| C$_4$H$_9$ | C$_4$F$_9$C$_2$H$_4$SC$_2$H$_4$N(CH$_3$)$_2$ | 92 | | |
| C$_6$F$_{13}$ | " | 95 | | |
| C$_4$F$_9$ | C$_6$F$_{13}$C$_2$H$_4$SC$_2$H$_4$N(CH$_3$)$_2$ | 90 | | |
| C$_6$F$_{13}$ | " | 91 | | |
| C$_6$F$_{13}$ | C$_8$F$_{17}$C$_2$H$_4$SC$_2$H$_4$N(CH$_3$)$_2$ | 90 | | |

TABLE B

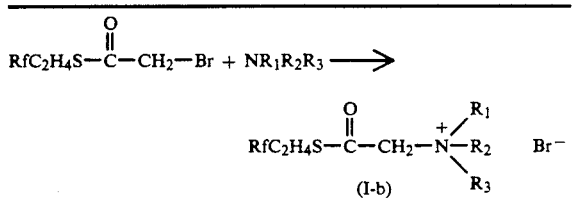

| | | COMPOUND I-b | | |
|---|---|---|---|---|
| Rf | Amine NR$_1$R$_2$R$_3$ | Yield (%) | γs | γi |
| C$_4$F$_9$ | N,N-Dimethylheptylamine | 92 | 22.5 | 5.9 |
| C$_6$F$_{13}$ | " | 91 | 17.2 | 3.2 |
| C$_8$F$_{17}$ | " | 72 | 18.8 | 6.1 |
| C$_4$F$_9$ | N,N-Dimethyloctylamine | 93 | 17.2 (k) | |
| C$_6$F$_{13}$ | " | 95 | 16.5 (i) | |

TABLE B-continued $$RfC_2H_4S-\overset{\overset{O}{\|}}{C}-CH_2-Br + NR_1R_2R_3 \longrightarrow$$

$$RfC_2H_4S-\overset{\overset{O}{\|}}{C}-CH_2-\overset{+}{N}\overset{R_1}{\underset{R_3}{\diagdown R_2}} \quad Br^-$$

(I-b)

| Rf | Amine NR₁R₂R₃ | Yield (%) | γs | γi |
|---|---|---|---|---|
| C₈F₁₇ | " | 70 | 17.0 | |
| C₄F₉ | N,N-Dimethylnonylamine | 88 | 17.1 | 1.0 |
| C₆F₁₃ | " | 91 | 16.8 | 3.0 |
| C₈F₁₇ | " | 75 | 17.7 | |
| C₄F₉ | N,N-Dimethyldecylamine | 93 | 18.7 | |
| C₆F₁₃ | " | 89 | 18.9 | |
| C₈F₁₇ | " | 78 | 15.8 (k) | |
| C₄F₉ | N,N-Dimethyldodecylamine | 91 | 18.7 | 0.7 |
| C₆F₁₃ | " | 92 | 16.5 | 0.7 |
| C₈F₁₇ | " | 72 | 16.0 (k) | |
| C₄F₉ | N-Allyl-N-methyloctylamine | 70 | 17.6 (k) | |
| C₆F₁₃ | " | 74 | 16.4 (k) | 0.8 |
| C₈F₁₇ | " | 66 | 15.6 (k) | |
| C₄F₉ | N-Allyl-N-methylnonylamine | 72 | 17.6 (k) | |
| C₆F₁₃ | " | 73 | 16.1 (k) | |
| C₈F₁₇ | " | 65 | 16.5 (k) | |
| C₄F₉ | N-Allyl-N-methyldecylamine | 68 | 18.1 (k) | |
| C₆F₁₃ | " | 72 | 16.0 (k) | |
| C₄F₉ | N-Allyl-N-methylundecylamine | 70 | 18.5 (k) | |
| C₆F₁₃ | " | 71 | 16.3 (k) | |
| C₄F₉ | N-Allyl-N-methyldodecylamine | 67 | 19.1 (k) | |
| C₆F₁₃ | " | 69 | 16.7 (k) | |
| C₄F₉ | C₄F₉C₂H₄SC₂H₄N(CH₃)₂ | 85 | | |
| C₆F₁₃ | " | 81 | | |
| C₄F₉ | C₆F₁₃C₂H₄SC₂H₄N(CH₃)₂ | 77 | | |
| C₆F₁₃ | " | 79 | 16.0 | 6.0 |
| C₈F₁₇ | " | 80 | | |
| C₄F₉ | C₈F₁₇C₂H₄SC₂H₄N(CH₃)₂ | 65 | | |
| C₆F₁₃ | " | 70 | | |
| C₈F₁₇ | " | 70 | | |
| C₄F₉ | N-Methyldioctylamine | 86 | | |
| C₆F₁₃ | " | 85 | | |
| C₄F₉ | 2-Dimethylaminoethyl methacrylate | 88 | | |
| C₆F₁₃ | 2-Dimethylaminoethyl methacrylate | 91 | | |
| C₈F₁₇ | 2-Dimethylaminoethyl methacrylate | 65 | | |

TABLE C $$RfC_2H_4NH\overset{\overset{O}{\|}}{C}CH_2Br + NR_1R_2R_3 \longrightarrow$$

$$RfC_2H_4NH\overset{\overset{O}{\|}}{C}CH_2\overset{+}{N}\overset{R_1}{\underset{R_3}{\diagdown R_2}} \quad Br^-$$

(I-c)

| Rf | Amine NR₁R₂R₃ | Yield (%) | γs | γi |
|---|---|---|---|---|
| C₆F₁₃ | N,N-Dimethylheptylamine | 88 | 15.4 | 1.5 |
| C₄F₉ | N,N-Dimethyloctylamine | — | 17.6 | 0.4 |
| C₆F₁₃ | " | 92 | 15.2 | 1.3 |
| C₆F₁₃ | N,N-Dimethylnonylamine | 82 | 15 | 1.2 |
| C₄F₉ | N,N-Dimethyldecylamine | — | | |
| C₆F₁₃ | " | 87 | 15.4 | 1.0 |
| C₄F₉ | N,N-Dimethyldodecylamine | — | | |
| C₆F₁₃ | " | 86 | 16.8 | 0.4 |

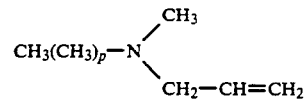

used in Example 5 were prepared in two stages. The first consists in reacting an excess of allylamine $CH_2=CH-CH_2-NH_2$ with the corresponding alkyl bromide $CH_3(CH_2)_p-Br$. The second consists in methylating the N-allylalkylamine thus obtained, $CH_3(CH_2)_p-NH-CH_2CH=CH_2$ with a formaldehyde/formic acid mixture. The operating procedure is as follows:

a) 0.3 moles of allylamine are placed in a reactor fitted with a magnetic stirrer, a condenser and a dropping funnel, and cooled in an ice bath. 0.1 mole of alkyl bromide is then added slowly. The mixture is then heated to 50° C. for 12 hours while being stirred. After addition of an aqueous solution of sodium hydroxide saturated with sodium chloride, the organic phase is extracted with ethyl ether. The ether phase is then dried over anhydrous sodium sulphate. The solvent is evaporated off. When the residue is distilled, the desired N-allylalkylamine is obtained and 0.2 moles of allylamine, which can be recycled, are recovered.

Table D, which follows, gives the yield and the boiling point of the various N-allylalkylamines $CH_3(CH_2)_p-NH-CH_2CH=CH_2$ thus obtained:

TABLE D

| P | 7 | 8 | 9 | 10 | 11 |
|---|---|---|---|---|---|
| Bp at 133 PA | 61° C. | 67° C. | 75° C. | 84° C. | 101° C. |
| Yld | 80% | 75% | 77% | 73% | 80% | b) 0.01 mole of N-allyalkylamine is introduced into a reactor fitted with a condenser and a dropping funnel and cooled to 0° C. Thereafter, 0.05 mole of formic acid and 0.03 mole of commercial formaldehyde in 35% strength aqueous solution are then added slowly in succession. The mixture is heated to 95°-100° C. for 12 hours. Then, after returning to ambient temperature, an aqueous sodium hydroxide solution saturated with sodium chloride is added. The organic phase is then extracted with ethyl ether and is then dried over sodium sulphate. The solvent is evaporated off. The residue is distilled under reduced pressure to give the N-allyl-N-methylalkylamine:

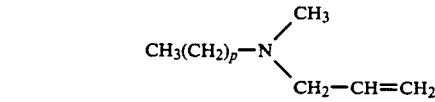

The following table gives the yield and the boiling point of the various N-allyl-N-methylalkyl-amines thus obtained:

TABLE E

| P | 7 | 8 | 9 | 10 | 11 |
|---|---|---|---|---|---|
| Bp at 133 PA | 56° C. | 58° C. | 72° C. | 79° C. | 99° C. |
| Yld | 98% | 99% | 90% | 95% | 97% |

EXAMPLE 6

The procedure is as in Example 5 (first case), using N,N,N',N'-tetramethylethylenediamine as amine and 2-perfluorohexylethylbromoacetamide: $C_6F_{13}-C_2-$ $H_4$—NH—CO—$CH_2$—Br, as bromide, with a bromide/diamine molar ratio equal to 2. Under these conditions, the double salt of formula:

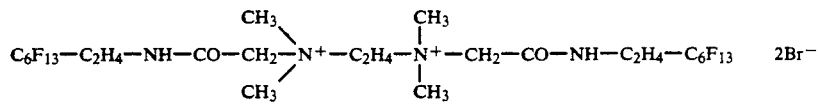

which melts at 215° C., is obtained in a 91% yield. $\gamma s = 14.8$ mN/m (0.1% aq. sol.).

When 2-perfluorobutylethylbromoacetamide: $C_4F_9$—$C_2H_4$—NH—CO—$CH_2$—Br is used, the following double salt is obtained:

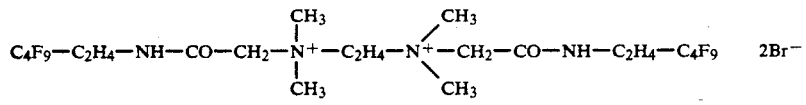

M = 210° C.  Yld = 87%  $\gamma s$ = 20.1 mN/m  (0.1% aq. sol.).

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims.

We claim:

1. A compound of the formula:

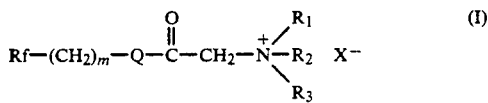

in which Rf denotes a linear or branched perfluoroalkyl radical containing from 2 to 16 carbon atoms, m is an integer ranging from 1 to 4, Q denotes an oxygen or sulphur atom or an NH group, $X^-$ denotes an monovalent anion or its equivalent, $R_1$ denotes an alkyl radical containing from 1 to 3 carbon atoms, $R_2$ denotes allyl or a linear or branched alkyl radical containing from 1 to 18 carbon atoms, and $R_3$ denotes a linear or branched alkyl radical containing from 7 to 18 carbon atoms or one of the following radicals:

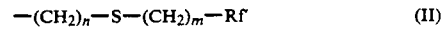

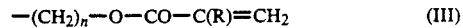

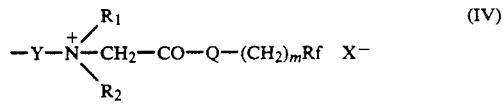

wherein m, $R_1$, $R_2$, Q, Rf and $X^-$ are such as defined above, n is an integer ranging from 2 to 4, R denotes hydrogen or methyl, Y denotes an alkylene bridge of 2 to 8 carbon atoms optionally interrupted by an oxygen atom, and Rf' denotes a perfluoroalkyl radical such as Rf.

2. A compound according to claim 1, wherein m is equal to 2.

3. A compound according to claim 1, wherein Rf and Rf' are linear perfluoroalkyl radicals containing 4, 6, 8 or 10 carbon atoms.

4. A method of using the compound according to claim 1 as a surface-active agent or as a monomer for the manufacture of artificial vesicles.

* * * * *